United States Patent [19]

Calenoff et al.

[11] Patent Number: 4,845,027
[45] Date of Patent: Jul. 4, 1989

[54] FLUOROMETRIC ASSAY OF ALLERGIC REACTIONS

[75] Inventors: Emanuel Calenoff, Burlingame; Ruth M. Johnson, Redwood City; Yuh-Geng Tsay, San Jose; John Scott, Mountain View, all of Calif.

[73] Assignee: Minnesota Mining and Manufacturing Company, St. Paul, Minn.

[21] Appl. No.: 144,737

[22] Filed: Jan. 15, 1988

Related U.S. Application Data

[63] Continuation of Ser. No. 434,061, Oct. 13, 1982, abandoned.

[51] Int. Cl.$^4$ .......................................... G01N 33/053
[52] U.S. Cl. .......................................... 435/7; 435/21; 436/513; 436/809
[58] Field of Search ...................... 435/7, 21; 436/513, 436/809

[56] References Cited

U.S. PATENT DOCUMENTS

| Re. 31,006 | 8/1982 | Schuurs et al. | 435/7 |
|---|---|---|---|
| 3,720,760 | 3/1973 | Bennich | 436/513 |
| 3,941,876 | 3/1976 | Marinkovich | 436/513 X |
| 4,002,532 | 1/1977 | Weltman | 436/513 X |
| 4,211,762 | 7/1980 | Huggins | 436/513 X |
| 4,240,751 | 12/1980 | Linnecke | 435/291 X |
| 4,331,650 | 5/1982 | Brewer | 436/513 |
| 4,347,311 | 8/1982 | Schmitz | 436/513 X |
| 4,376,110 | 3/1983 | David et al. | 436/513 |
| 4,450,231 | 5/1984 | Ozkan | 436/539 |
| 4,501,970 | 2/1985 | Nelson . | |

FOREIGN PATENT DOCUMENTS

83/306178.1 10/1982 European Pat. Off. .

OTHER PUBLICATIONS

"Enzyme-Immunoassay", Maggio, E. T., ed., pp. 26, 173-178, 186, CRC Press, Inc., Boca Raton, 1980.
"Automated Immunoanalysis", Part 2, R. F. Ritchie, ed., pp. 335-342, Marcel Dekker, Inc., New York, 1978.
Poulson et al., *Vox Sang.*, 23:107-118, (1972).
Poulson et al., *BIOCHEMICA ET BIOPHYSICA ACTA*, 82:463-475, (1964).
Voller, A., et al.; Brief Communication, WHO 51:209-211, (1974).
Voller, A., Chapt. 9, "Heterogenaous Enzyme-Immunoassays and the Applications", pp. 181-196, in *Enzyme Immunoassay*, (E. Maggio, ed., CRC Press, Boca Raton, Fla., 1980).
Shalev, A., et al.; J. Immuno. Methods, 38:125-139, (1980).
Hellsing, K., et al., Chapt. 3, pp. 67-112, Automated Immunoanalysis (Marcel Dekker, New York), 19.
Ceska, M., et al., Eur. J. Immunol., 2:58-62, (1972).
Bulter, J. E., Chapt. 2, "Antibody-Antigen and Antibody"—Hapten Reactions, pp. 5-52, in *Enzyme Immunoassay*, (E. Maggio, Ed., CRC Press, Buca Raton, Fla., 1980).
Clark, B. et al., Chapt. 8, "Enzyme Linked Immunosorbent Assay (ELISA): Theoretical and Practical Aspects", pp. 167-179 in *Enzyme Immunoassay*, (E. Maggio, Ed., CRC Press, Boca Raton, Fla., (1980).
Mattiasson, B., et al., Chapt. 11, "Novel Approaches to Enzyme Immunoassay", pp. 213-248 in *Enzyme Immunoassay*, (E. Maggio, Ed., CRC Press, Boca Raton, Fla., 1980).

*Primary Examiner*—Christine M. Nucker
*Attorney, Agent, or Firm*—Donald M. Sell; Walter N. Kirn; Philip M. Goldman

[57] ABSTRACT

A method for identifying and quantifying allergen specific IgE levels in patient serum by conjugating the serum IgE with allergens on an insoluble support, conjugating the serum IgE with an enzyme labeled anti-IgE antibody, contacting the enzyme with a solution of a substrate which will yield a fluorescent product in the presence of the enzyme, and measuring the level of fluoresence in the solution.

8 Claims, No Drawings

FLUOROMETRIC ASSAY OF ALLERGIC REACTIONS

This is a continuation of application Ser. No. 434,061 filed Oct. 13, 1982.

FIELD OF THE INVENTION

This invention relates to methods and reagents for assaying blood serum of patients demonstrating allergic symptomotology to identify the source of the allergy and determine the level of the respective allergen specific IgE in the serum. In particular, this invention relates to diagnostic methods and reagents therefore which provide increased specificity and accuracy, the results of which can be reliable used as a basis for determining desensitization dose regimens to be used to in treating patients for allergic reactions.

BACKGROUND OF THE INVENTION

Description of the Prior Art

Radiometric and fluorometric methods for identifying and measuring allergy specific IgE levels in patient serum are commercially available and are known as the RAST test, for example. U.S. Pat. Nos. RE-29,474; 3,555,143; 3,648,346; 3,720,760 and 3,966,898 relate to these methods and reagents therefor. Enzymatic immunological methods for identifying and quantifying antigens and antibodies in liquids are widely used and are known as the ELISA and EIA, for example. Basic technology for enzymatic assays and reagents therefor is disclosed in U.S. Pat. Nos. RE-29,169 and 3,839,153, for example.

A review of the current state of the art with regard to immunoassays for the detection of proteins in solutions is provided by R. Rose et al, *Manual of Clinical Immunology,* 2nd ed. American Society for Microbiology, Washington, pp 327–429, 775–849 (1980) and by A. Voller et al, Immunoassays for the 80's, University Park Press, Baltimore (1981), and the publications cited therein, the entire contents of both publications being hereby incorporated by reference. The chapter therein by T. A. E. Platts-Mills et al, "Radioimmunoassays in Allergy", pp 289–311, and the publications cited therein provide a comprehensive review of the field of this invention.

SUMMARY OF THE INVENTION

This invention relates to a method for identifying and quantifying allegen specific IgE levels in patient serum. It comprises the steps of first contacting an insoluble support having allergen adhering thereto with patient serum for a sufficient time to permit conjugation of allergen with IgE in the patient serum. The patient serum is then removed from the support. Secondly, the insoluble support is contacted with an anti-IgE antibody labeled with a fluorogenic enzyme (i.e., an enzyme by means of which suitable substrate will undergo chemical reaction to yield fluorescent products) for sufficient time to permit conjugation of serum IgE conjugated with allergen on the insoluble support with the anti-IgE antibody. The unconjugated anti-IgE antibody is then removed from the support. Thirdly, the solid support is contacted with a solution of a substrate which undergoes chemical reaction to yield a fluorescent product when in the presence of the fluorogenic enzyme, the contact being continued for sufficient time to yield fluorescent product. The level of fluorescence in the solution is then measured.

In preferred embodiments of this invention, the allergen is bonded to the surface of the insoluble support by noncovalent bonding such as by absorption or adsorption, for example, or by covalent bonding; the insoluble support has a plurality of test wells separated by opaque material; the anti-IgE antibody is a monoclonal antibody to which alkaline phosphatase is bound; and the anti-IgE is contacted with the insoluble support in an aqueous solution containing from 1 to 8 weight percent polyethylene glycol having a molecular weight of from 1000 to 10,000; and the substrate is 4-methylumbelliferyl phosphate.

DETAILED DESCRIPTION OF THE INVENTION

Key to successful treatment of allergic conditions is the accurate identification of the offending allergen and the titration of the patient to determine the desensitization dosage. In general, reconstituted allergen extract is injected in sufficient quantity to cause major production of antigen-specific IgG (blocking antibody) and major production and/or activation of suppressor T lymphocytes. However, the quantity should not be sufficient to cause major allergic reaction and excessive antigen-specific IgE production. To the extent that antigen-specific IgE is produced at an increased level, it is critical that the IgG and suppressor IgE production be in such balance as to prevent allergic reaction.

The concentration and amount of the desensitization dosage are dependent upon many factors which are specific to the patient undergoing the allergic reaction. It is, therefore, necessary to titrate the patient to determine the proper dosage. A variety of standard techniques are available to carry out this procedure. Examples of traditional procedures are described in *Remington's Pharmaceutical Sciences,* supra, pp 1344–1352, the entire contents of which are incorporated herein by reference. However, the methods available prior to this invention have lacked the specificity and accuracy to be more than a rough approximation of the order of magnitude of the appropriate beginning dose range.

The method of this invention provides the specificity and accuracy to determine a suitable desensitization dosage, particularly when the allergen used for desensitization and the allergen component of the diagnostic method have the same allergen profile and specificity. After identification of the offending allergen and quantification of the offending allergen, standard desensitization immunotherapy procedures are employed. The procedure normally used involves injecting into the patient gradually increased doses of the allergen, usually to maximum tolerated doses (doses not giving rise to major allergic response), at varying intervals in an attempt to develop IgG antibody protection against the agents and to increase the specific suppressor T lymphocyte activity. With the method of this invention, more exact assessment of the suitable desensitization dose can be initially determined, making unnecessary the exacting procedures formerly required. The exact mechanisms of this treatment are not fully understood. Booster injections to maintain the requisite IgG and suppressor T lymphocyte levels are required at intervals of one to four weeks. Usually the doses required for booster injections are substantially greater than the maximum dose required for control of the initial allergic reaction.

The process of this invention comprises a first step of contacting an insoluble support having allergen adhering thereto with patient serum for a sufficient time to permit conjugation of allergen with IgE in the patient serum and then removing the patient serum from the support. In this procedure the patient serum is preferably undiluted prior to contact with the supported allergen. The incubation time should be sufficient to permit substantial conjugation to occur, the time being temperature dependent. Suitable incubation times are from 30 to 180 minutes at temperatures within the range of from 18° to 40° C., the preferred contact time being from 60–120 minutes at temperatures within the range of from 20° to 26° C.

The insoluble support having the allergen adhering thereto is an important aspect of this invention. The allergen can be any allergenic material such as allergen derived from pollens derived from trees, shrubs, weeds, and grasses; molds; smuts; dusts; allergens derived from danders, hair, and epidermals of animals; extracts derived from insects including insect venoms; and from foods.

A wide variety of compounds can be employed as the solid support, the primary consideration being the binding of the allergens to the surface, the absence of interference with the enzyme labeled anti-IgE antibody reagent, enzymatic reaction thereof with a substrate and fluorescent properties of the enzymatic reaction product. A wide variety of organic and inorganic polymers, both natural and synthetic can be employed as the solid support. Exampes of suitable polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrose cellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be employed as the insoluble support are silica gel, silicon wafers, glass, paper, insoluble protein, metals, metaleoids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12–24 carbon atoms) alkyl amonium salts and the like.

A preferred diagnostic support of this invention comprises a polystyrene or styrene-(vinyl monomer) co-polymer having the allergenic extract bound thereto by adsorption, ionic bonding, van der Waals adsorption, electrostatic bonding, other non-covalent bonding, or covalent bonding. A particularly advantageous support for this procedure comprises a microtiter plate having a plurality of wells. The well surface or plastic cup inserts therein can constitute the allergen support. Most advantageously, the microtiter plate or the well inserts are opaque to light so that excitation light applied to a well or fluorescence generated in response thereto does not reach or influence contents of the surrounding wells. With this system each well can be employed as a test system independent of the other wells.

A variety of procedures are known for which are suitable for adhering allergens to insoluble supports. Suitable procedures are described by Ichiro Chibata in *Immobilized Enzymes,* , Halsted Press, New York, 1978, and by A. Cuatrecasas, *J. Bio. Chem.* 245 3059(1970), the entire contents of which are hereby incorporated by reference.

In a procedure for non-covalent adhesion of allergen to the surface of an insoluble support, the allergenic material can be applied to the surface of a polystyrene microtiter well or polystyrene individual insert well therefor in an aqueous buffer solution. The polystyrene surface is initially cleaned with a cleaning fluid such as methanol and dried. The buffered allergen solution is placed in the well or insert cup and incubated at room temperature until adsorption occurs, for example for 2 hours at room temperature. The well is then rinsed with a weak saline solution and dried.

Alternatively, the well therefor can be coated with a protein and coupled with allergen using the procedures described in U.S. Pat. No. 4,210,418 using glutaraldehyde as a coupling agent, for example. In a still further procedure, the well can be coated with a layer having free isocyanate groups such as a polyether isocyanate, and application of the allergen in aqueous solution thereto effects the requisite bonding. In a still further procedure, the allergen can be coupled to a hydroxylated material by means of cyanogen bromide as described in U.S. Pat. No. 3,720,760.

The preferred allergens and supports therefor are those described in commonly assigned copending patent application Ser. No. 433,962 entitled STABLE ANTIGENIC EXTRACTS AND METHODS filed on the even day herewith.

After conjugation of serum IgE with allergen adhering to the insoluble support has occurred, the patient serum is removed therefrom. Surplus liquid is removed and the solid surface is then rinsed with a suitable, conventional buffered solution such as a weak saline solution containing a surfactant such as a polyoxyethylene oxide sorbitan ester of a fatty acid such as polyoxyethylene sorbitan monooleate.

The second step of the process of this invention comprises contacting the insoluble support with an anti-IgE antibody labeled with a fluorogenic enzyme. The incubation is continued for sufficient time to permit serum IgE conjugated with allergen (if any) on the insoluble support to conjugate with the anti-IgE antibody. After incubation, the excess liquid is removed, and the surface of the insoluble support is rinsed with a weak saline solution as described above with respect to the first step to remove unconjugated antibody.

IgE antibodies are available from many sources, and the methodology for producing them is well known and is described in several of the patents and publications cited above. The preferred antibodies are monoclonal antibodies. The technology for making monoclonal antibodies is well developed, and the procedures suitable for making monoclonal anti-IgE antibodies are described by D. Catty, et al in "Antisera in Immunoassays with special Reference to Monoclonal Antibodies to Human Immunoglobulins", *Immunoassay's for the 80's,* supra, pp 133–153 and the publications cited therein, the entire contents of which are hereby incorporated by reference.

Fluorogenic enzymes and methods for bonding them to antibodies without impairing the ability of the antibody to selectively conjugate with antigen are well known in the art. Suitable enzymes and procedures for coupling them to antibodies are described in U.S. Pat. No. 4,190,496, for example, the contents thereof being hereby incorporated by reference. The preferred fluorogenic enzymes and the suitable substrates corresponding thereto include horseradish peroxidase (substrate—homovanillic acid or 4-hydroxy-3-methoxyphenylacetic acid); alkaline phosphatase (substrate—4-methylumbelliferyl-beta-D-galactoside and other umbelliferones), for example.

The enzyme labeled anti-IgE antibody is applied to the insoluble support in an aqueous solution. The solution preferably contains suitable salts and buffers to preserve the reactants and facilitate the conjugation reaction. For example, the solution can contain bovine serum albumin (BSA), phosphate buffer solution (PBS), and a mild surfactant such as a polyoxyethylene sorbitan ester employed in the rinse solutions described above.

Particularly preferred ingredients in the anti-IgE solution are the polyethylene glycols having molecular weights of from 1000 to 8000 and preferably from 2000 to 4000 in concentrations of from 1 to 8 and preferably from 2 to 6 weight percent. Polyethylene glycols greatly increase the speed and sensitivity of the reaction.

With the preferred anti-IgE solutions of this invention, the incubation time of the solutions with the insoluble support is temperature dependent. At temperatures of 18° to 40° C., incubation times of at least from 30 to 180 minutes can be used. The preferred temperatures are within the range of from 20° to 26° C., and at these temperatures, incubation times from 60 to 120 minutes can be employed. It should be appreciated that prolonged incubation times in any of the steps of this invention can reduce the efficacy of the process. Since rapid analysis is an objective of this invention, the lowest times which still yield the desired accuracy are preferred.

The third step of the process of this invention comprises contacting the solid support with a solution of a substrate which undergoes chemical reaction in the presence of the fluorogenic enzyme for a time sufficient for fluorescent compounds to be formed. Suitable substrates and the enzymes they are converted by are known in the art and are described in U.S. Pat. No. 4,190,496, for example. Examples of substrates have been described hereinabove with respect to the corresponding fluorogenic enzyme.

The solid is contacted with an aqueous solution of the substrate containing from $10^{-2}$ to $10^{-6}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reaction product to form. At temperatures of from 18° to 40° C., incubation times of from 5 to 240 minutes can be used. Preferably, the temperature is within the range of from 20° to 26° C., and the incubation time is from 30 to 90 minutes.

The equipment and procedures for determining the level of fluorescence in the substrate solutions are those conventionally employed in the art. The level of fluoresence is a function of the enzyme concentration on the insoluble support which is, in turn, a function of the allergen specific IgE level in the patient serum. By comparing the fluoresence level with the levels measured by carrying out the procedure with control solutions containing known concentrations of the respective allergen specific IgE, the precise concentration of the corresponding IgE antibody in the patient serum can be determined.

This invention is further illustrated by the following specific but non-limiting examples. Temperatures are given in degrees Centigrade and concentrations are given as weight percents unless otherwise specified.

EXAMPLE 1

In this example, allergen derived from Perennial Ryegrass is adhered to a well of a black, opaque polystyrene microtiter plate. The well is washed with methanol and dried. A 1:200 dilution of a 1:10 extract from Perennial Ryegrass Pollen (a 1:10 extract contains about 100,000 allergy units by the FDA suggested standards) in phosphate buffered saline having a pH of 7.5 is prepared, and 100 microliters of extract solution is pipetted into the well. After incubation for 2 hours at room temperature, the excess liquid is removed, and the well is washed 3 times with a 5 to 10% aqueous solution of sucrose or sorbitol and dried.

EXAMPLE 2

Repeating the procedure of Example 1 with allergens derived from each of the following tree pollens provides a microtiter well to which the corresponding allergen is adhered: Acacia -*Acacia longifolia;* Acacia, Bailey's *Acacia baileyana;* Ailanthus (See Tree of Heaven)—*Ailanthus altissima;* Alder, Mountain (Tag) (Slender)—*ainus tenuifolia*/incana; Alder, Red (Oregon-)—*Alnus rubra;* Alder, Sitka—*Alnus sinuata;* Alder, White—*Alnus rhombifolia;* Almond—*Prunus amygdalus;* Apple—*Pyrus malus (Malus pumila);* Apricot—*Prunus armeniaca;* Arbor Vitae, Oriental (Ornamental-)—*Thuja orientalis;* Ash, Arizona (Velvet)—*Fraxinus velutina;* Ash, Blake—*Fraxinus nigra;* Ash, Green (Red-)—*Fraxinus pennsylvanica;* Ash, Oregon—*Fraxinus oregona* (latifolia); Ash, White—*Fraxinus americana;* Aspen—*Populus tremuloides;* Bayberry (Sweet Gale)—*Myrica gale;* Beech, American—*Fagus grandifolia;* Birch, Cherry—*Betula lenta;* Birch, Paper—*Betula papyrifera;* Birch, River (Black or Red-)—*Betula nigra;* Birch, Spring—*Betula fontinalis;* Birch, White (Weeping)—*Betula pendula;* Birch, Yellow—*Betula lutea;* Blue Beech *(Am. Hornbeam)*—Carpinus carolineana; Bottle Brush—*Callistemon citrinus;* Box Elder—*Acer negundo;* Butternut—*Juglans cinerea;* Carob Tree—*Ceratonia siliqua;* Cedar, Deodar—*Cedrus deodora;* Cedar, Giant—*Thuja plicata;* Cedar, Incense—*Linocedrus decurrens;* Cedar, Japanese—*Cryptomeria japonica;* Cedar, Port Orford (Lawson Cypress)—*Chamaecyparis lawsoniana;* Cedar, Mountain—*Juniperus sabinoides (Juniperus asheii);* Cedar, Red—*Juniperus virginiana;* Cedar, Rocky Mountain—*Juniperus scopulorum;* Cedar, Salt (Tamarisk)—*Tamarix gallica;* Cedar, White—*Thuja occidentalis;* Cherry, *Prunus cerasus;* Chestnut, American—*Castanea dentata;* Chestnut, Horse—*Aesculus hippocastanum;* Cottonwoo, Black (Poplar, Western Balsam)—*Populus trichocarpa;* Cottonwood, Common—*Populus deltoides;* Cottonwood, Fremont—*Populus fremontii;* Cypress, Arizona—*Cupressus arizonica;* Cypress, Bald (White)—*Taxodium distichum;* Cypress, Italian—*Cupressus sempervirens;* Cypress, Monterey—*Cupressus macrocarpa;* Elderberry—*Sambucus glauca;* Elm, American—*Ulmus ameri-* cana; Elm, Cedar (Fall Blooming)—*Ulmus crassifolia;* Elm, Chinese—*Ulmus parvifolia;* Elm, Siberian—*Ulmus pumila;* Elm, Slippery—*Ulmus fulva* (rubra); Eucalyptus (Blue Gum)—*Eucalyptus globulus;* Fir, Douglas—*Pseudotsuga menziesii;* Fir, Red (Noble)—*Abies nobilis* (procera); Fir, White—*Abies concolor;* Gum, Sweet—*Liquidambar styraciflua;* Hackberry Celtis occidentalis; Hazelnut, American—*Corylus americana;* Hemlock, Eastern—piTsuga canadensis; Hemlock, Western—*Tsuga heterophylla;* Hickory, Shagbark—*Carya ovata;* Hickory, Shellbark—*Carya laciniosa;* Hickory, White—*Carya tomentosa;* Ironwood (Hop-Hornbeam)—*Ostrya virginiana;* Juniper, California—*Juniperus californica;* Juniper, Chinese—*Juniperus chinensis;* Juniper, Oneseed—*Juniperus monosperma;* Juniper, Pinchot—*Juniperus pinchotti;* Juniper, Utah—*Juniperus osteosperma (juniperus utahensis);* Juniper, Western—*Juniperus occidentalis;* Lilac—*Syringa vulgaris;* Linden (Basswood)—*Tilia americana;* Locust, Black—*Robinia* pseudoacacia; Maple, Big-Leaf (Coast)—*Acer macrophyllum;* Maple, Hard (Sugar)—*Acer saccharum;* Maple, Red—*Acer* rubrum; Maple, Soft (Silver)—*Acer saccharinum;* Melaleuca (Punk Tree)—*Melaleuca leucadendron;* Mesquite—*Prosopis juliflora;* Mock Orange, Wild (Syringa)—*Philadelphus lewisii;* Mulberry, Paper—*Broussonetia papyifera;* Mulberry, Red—*Morus rubra;* Mulberry, White—*Morus alba;* Oak, Arizona (Gambel)—*Quercus gambelii;* Oak, Arizona Scrub (Canyon)—*Quercus chrysolepsis;* Oak, Black (Yellow)—*Quercus velutina;* Oak, Black Jack—*Quercus marilandica;* Oak, Bur—*Quercus macrocarpa;* Oak, California Black—*Quercus kelloggii-californica;* Oak, California Scrub *Quercus dumosa;* Oak, Coast Live—*Quercus agrifolia;* Oak, Engelmann—*Quercus engelmanii;* Oak, Garry (Western White)—*Quercus garryana;* Oak, Holly—*Quercus ilex;* Oak, Interior Live—*Quercu wislizenii;* Oak, Post—*Quercus stellata;* Oak, Red—*Quercus rubra;* Oak, Swamp (Pin)—*Quercus palustris;* Oak, Valley—*Quercus lobata;* Oak, Virginia Live—*Quercus virginiana;* Oak, Water—*Quercus nigra;* Oak, White—*Quercus alba;* Olive—*Olea europaea;* Orange—*Citrus* sinensis; Osage Orange—*Maclura pomifera;* Palm, Date—*Phoenix dactylifera;* Palm, Dwarf—*Chamaerops humulis;* Palm, Canary Island Date (Ornamental)—*Phoenix canariensis;* Palm, Queen—*Cocos plumosa;* Peach—*Prunus persica;* Pear—*Pyrus communis;* Pecan—*Carya pecan;* Pepper Tree, California—*Schinus molle;* Pepper Tree, Brazilian—*Schinus terebinthifolius;* Pine, Australian (Beefwood)—*Casuarina equisetifolia;* Pine, Austrian—*Pinus nigra;* Pine, Canary Island—*Pinus canariensis;* Pine, Digger—*Pinus sabiniana;* Pine, Loblolly—*Pinus taeda;* Pine, Lodgepole—*Pinus contorta;* Pine, Monterey—*Pinus radiata;* Pine, Pinyon—*Pinus edulis;* Pine, Red (Norway)—*Pinus resinosa;* Pine, Shortleaf—*Pinus echinata;* Pine, Virginia Scrub—*Pinus virginiana;* Pine, Western Yellow—(Ponderosa) *Pinus ponderosa;* Pine, White (Eastern)—*Pinus strobus;* Pine, White (Western)—*Pinus monticola;* Plum (Prune)—*Prunus domestica;* Poplar, Balsam—*Populus balsamifera;* Poplar, Lombardy—*Populus nigra-italica;* Western Balsam (See Cottonwood, Black) *Populus trichocarpa;* Poplar, White—*Populus* alba; Privet—Ligustrum spp.; Redwood—*Sequoia sempervirens;* Russian Olive—*Elaeagnus angustifolia;* Spruce, Red—*Picea rubens;* Spruce, Sitka—*Picea sitchensis;* Sycamore, American (Eastern)—*Platanus occidentalis;* Sycamore, Mapleleaf—*Platanus acerifolia;* Sycamore, Western—*Platanus racemosa;* Tamarack (Larch)—*Larix occidentalis;* Tamarisk (See Cedar, Salt)—*Tamarix gallica;* Tree of Heaven—*Ailanthus altissima;* Walnut, Arizona—*Juglans rupestris;* Walnut, Black—*Juglans nigra;* Walnut, Hind's California Black—*Juglans hindsii;* Walnut, So. California Black—*Juglans californica;* Walnut, English—*Juglans regia;* Willow, Arroyo—*Salix lasiolepis;* Willow, Black—*Salix nigra;* Willow, Pussy—*Salix discolor;* Willow, Red—*Salix laevigata;* Willow, Yellow—*Salix lasiandra*

EXAMPLE 3

Repeating the procedure of Example 1 with allergens derived from each of the following grass and weed pollens provides a microtiter well to which the corresponding allergen is adhered: Bahia Grass—*Paspalum notatum;* Barley, Cultivated—*Hordeum vulgare;* Bent Grass, Colonial—*Agrostis tenuis;* Bermuda Grass—*Cynodon dactylon;* Bluegrass, Annual—*Poa annua;* Bluegrass, Canada—*Poa compressa;* Bluegrass, kentucky (June)—*Poa pratensis;* Bluegrass, Sandberg—*Poa sandbergii;* Brome Broncho-Ripgut—*Bromus rigidus;* Brome, California -*Bromus carinatus;* Brome, Cheat—*Bromus secalinus;* Brome, Smooth—*Bromus inermis;* Brome, Soft Cheat—*Bromus mollis;* Bunch, Blue (Northwestern Bunch)—*Agropyron spicatum;* Canarygrass—Phalaris canariensis; Canarygrass, Reed —*Phalaris arundinacea;* Corn, Cultivated—*Zea mays;* Fescue, Meadow (Tall)—*Festuca elatior;* Fescue, Red —*Festuca rubra;* Grama Grass, Blue (Side Oats)—*Bouteloua gracilis;* Johnson Grass—*Sorghum halepense;* Koeler's Grass (Western Junegrass) —*Koeleria cristata;* Lovegrass, Hawaiian—*Eragrostis variabilis;* Oats, Common Cultivated —*Avena sativ;* Oatgrass, Tall —*Avena elatior (Arrhenatherum elatius);* Orchard Grass —*Dactylis glomerata;* Quack Grass —*Agropyron repens;* Redtop —*Agrostis alba;* Rye, Cultivated —*Secale cereale;* Ryegrass, Alkali—*Elymus triticoides;* Ryegrass, Giant Wild—*Elymus cinereus;* Ryegrass, Italian —*Lolium multiflorum;* Ryegrass, Western—*Elymus glaucus;* Salt Grass—*Distichlis stricta;* Sorghum, Common Cultivated—*Sorghum vulgare;* Sudan Grass —*Sorghum vulgare* var. sudanese; Sweet Vernal grass—*Anthoxanthum odoratum;* Timothy—*Phleum pratense;* Velvetgrass—*Holcus Ianatus;* Wheat, Cultivated—*Triticum aestivum;* Wheatgrass, Crested—*Agropyron cristatum;* Wheatgrass, Western—*Agropyron smithii;* Alfalfa—*Medicago sativa;* Aster—*Aster sinensis;* Balsam Root—*Balsamorhiza sagittata;* Bassia—*Bassia hyssopifolia;* Beach Bur—*Franseria bipinnatifida;* Burro Brush (Greasebush)—*Hymenoclea salsola;* Careless Weed—*Amaranthus palmeri;* Castor Bean—*Ricinus communis;* Cattail, Broadleaf—*Typha latifolia;* Clover, Red *Trifolium pratense;* Clover, Sweet, Yellow—*Melilotus officinalis;* Clover, White (Dutch)—*Trifolium repens* (album); Cocklebur, Common—*Xanthium strumarium;* Cocklebur, Spiny—*Xanthium spinosum;* Cosmos—*Cosmos bipinnatus;* Daffodil—*Narcissus pseudo-narcissus;* Dahlia—*Dahlia pinnata* x *coccinea;* Daisy/ Chrysanthemum (Oxeyed Daisy)—*Chrysanthemum leucanthemum;* Dandelion—*Taraxacum officinale;* Dock, Bitter—*Rumex obtusifolius;* Dock, Yellow (Curly) Rumex crispus; Dog Fennel (Mayweed)—*Anthemix cotula;* Fireweed, Alaska—*Epilobium angustifolium;* Gladiolus—*Gladiolus Xhortulanus;* Goldenrod—Solidago spp; Greasewood—*Sarcobatus vermiculatus;* Hemp—*Cannabis sativa;* Hops—*Humulus lupulus;* Hopsage—*Grayia spinosa;* Iodine Bush (Burro Weed)—*Allenrolfea occidentalis;* Kochia (Mex. Fire-bush)—*Kochia scoparia;* Lamb's Quarters (Goosefoot)—*Chenopodium album;* Lily, Easter—*Lilium longiflorum;* Marigold—*Tagetes patula;* Marshelder, Burweed (Giant Poverty)—*Iva Xanthifolia;* Marshelder, Narrowleaf (August)—*Iva angustifolia;* Marshelder, True (Rough)—*Iva ciliata;* Mexican Tea—*Chenopodium ambrosioides;* Mustard, Black—*Brassica nigra;* Mustard, Common Yellow—*Brassica campestris;* Nettle—*Urtica dioica* (gracilis); Pickleweed—*Salicornia ambigua;* Pigweed, Rough Redroot—*Amaranthus retroflexus;* Pigweed, Spiny—*Amaranthus spinosus;* Plantain, English (Black)—*Plantago Ianceolata;* Poppy, California—*Eschoscholzia californica;* Povertyweed, Small—*Iva axillaris;* Rabbit Brush—*Chrysothamnus nauseosus;* Rabbit Bush (Bur Ragweed)—*Franseria deltoides;* Ragweed, Canyon—*Franseria ambrosioides;* Ragweed, Desert—*Franseria dumosa;* Ragweed, False—*Franseria acanthicarpa;* Ragweed, Giant—*Ambrosia trifida;* Ragweed, Short—*Ambrosia artemisiifolia* (elatior); Ragweed, Silver—*Dicoria canescens;* Ragweed, Slender—*Franseria tenuifolia;* Ragweed, Southern—*Ambrosia bidentata;* Ragweed, *Ambrosia psilostachya;* Rose—*Rosa multiflora;* Russian Thistle—*Salsola kali* (pestifer); Sagebrush—Annual—*Artemisia annua;* Sagebrush, Coast—*Artemisia californica;* Sagebrush, Common—*Artemisia tridentata;* Sagebrush, Green (Tarragon)-*Artemisia dracunculus;* Sagebrush, Mugwort—*Artemisia vulgaris* heterophylla; Sagebrush, Pasture (Carpet)—*Artemisi frigida;* Sagebrush, Sand Dune—*Artemisia pycnocephala;* Sagebrush, White (Prairie)—*Artemisia Iudoviciana;* Saltbush, Annual—*Atriplex wrightii;* Scale, All—*Atriplex polycarpa;* Scale, Bract—*Atriplex serenana bracteosa;* Scale, Brewers—*Atriplex lentiformis breweri;* Scale, Lens—*Atriplex lentiformis;* Scale, Red—*Atriplex rosea;* Scale, Silver (Fogweed)—*Atriplex argentea expansa;* Scale, Spear—*Atriplex patula hastata;* Scale, Wing (Shad)—*Atriplex canescen;* Scotch Broom—*Cytisus scoparius;* Sea Blite, California—*Suaeda californica;* Sedge—*Carex barbara;* Sheep Fat—*Atriplex confertifolia;* Sheep Sorrel—*Rumex acetosella;* Snapdragon—*Antirrhinum majus;* Suaeda (See Sea Blite); Sugar Beet—*Beta vulgaris;* Sunflower—*Helianthus annuus;* Waterhemp, Western—*Acnida tamariscina;* Winter Fat—*Eurotia lanata;* Wormseed (Jerusalem Oak)—*Chenopodium botrys;* Wormwood, Absinthe—*Artemisia absinthium.*

EXAMPLE 4

Repeating the procedure of Example 1 with allergens derived from each of the following epidermals and glandular extracts provides a microtiter well to which the corresponding allergen is adhered: Camel Hair & Dander; Cat Hair & Epithelium; Cattle Hair & Dander Deer Hair & Dander; Dog Hair & Dander; Feathers, Chicken; Feathers, Duck; Feathers, Goose; Feathers, Parakeet; Feathers, Pigeon; Feathers, Turkey; Fox Fur; Gerbil Hair & Epithelium; Glue, Fish; Goat Hair & Dander; Guinea Pig Hair & Dander; Hamster Hair & Epithelium; Hog Hair & Dander; Horse Hair & Dander; Human Hair; Mink Fur; Mohair; Monkey Hair & Epithelium; Mouse Hair & Epithelium; Poodle Hair & Dander; Pyrethrum; Rabbit Hair & Epithelium; Rat Hair & Epithelium; Seal Fur; Wool, Sheep.

EXAMPLE 5

Repeating the procedure of Example 1 with allergens derived from each of the following miscellaneous dusts provides a microtiter well to which the corresponding allergen is adhered: Acacia Gum; Alfalfa Hay; Algae, Chlorella spp.; Carragheen Gum; Coconut Fiber; Cotton Linters; Cotton-seed; Dust, Barley; Dust, Corn; Dust, Grain Mill; Dust, Mattress; Dust, Oat; Dust, Pea; Dust, Rye; Dust, Soybean; Dust, Upholstery; Dust, Wheat; Dust, Wood—Cedar/Juniper; Dust, Wood—fir/Hemlock; Dust, Wood—Gum; Dust, Wood—Mahogany; Dust, Wood—Maple; Dust, Wood—Oak Mix; Dust, Wood—Pine Mix; Dust, Wood—Redwood; Dust, Wood—Spruce; Dust, Wood—Walnut; Fern Spores, sp.; Flax Fiber ; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; Tobacco, Leaf.

EXAMPLE 6

Repeating the procedure of Example 1 with allergens derived from each of the following foods provides a microtiter well to which the corresponding allergen is adhered: Allspice; Almond; Apple Mix; Apricot Food; Arrowroot; Artichoke; Asparagus; Avocado; Banana; Barley, Whole (Grain); Bay Leaf; Bean, Kidney; Bean, Lima; Bean, Navy; Bean, Pinto-Frijole; Bean, String/Wax; Beef; Beet; Black-Eyed Pea; Blueberry; Brazil Nut; Buckwheat; Carrot; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Corn, Whole (Grain); Crab; Cranberry; Cucumber; Curry Powder; Date; Dill; Egg White; Egg, Whole; Egg, Yolk; Eggplant; Endive; Garlic; Gelatine; Ginger; Grape/Raisin Mix; Grapefruit; Haddock; Halibut; Hazelnut (Filbert); Herring; Honey; Hops Food; Horseradish; Lamb; Lemon; Lentil; Lettuce Mix; Lime; Liver, Beef (Calves); Lobster; Mackerel; Malt; Mangoes; Maple, Syrup/Sugar; Melon, (see Muskmelon Mix); Milk, Cow's (Whole); Milk, Cow's (Albumin); Milk, Cow's (Casein); Milk, Cow's (Whey); Milk, (Evaporated); Milk, Goat's; Mint Mix (Peppermint/ Spearmint); Mushroom; Mustard; Nutmeg; Oat, Whole (Grain); Okra; Olive Mix; Onion; Orange, Mandarin/Tangerine; Orange, Sweet; Oregano; Oyster Mix; Papaya; Paprika; Parsley; Parsnip; Pea; Peach Food; Peanut; Pear Food; Pecan Food; Pepper, Black/-White; Pepper, Bell (Green/Red); Perch, Lake; Pineapple; Plum/Prune Mix; Poppy Seed; Pork; Potato, Sweet/Yam; Potato, White; Pumpkin; Rabbit Meat; Radish; Raspberry; Snapper; Rhubarb; Rice, Whole (Grain); Rice, Wild; Rye, Whole (Grain); Safflower Seed; Sage; Salmon; Scallops; Sesame Seed; Shrimp; Sole; Soybean, Whole (Grain); Spinach; Squash, Mix; Strawberry; Sugar (Beet); Sugar (Cane); Sunflower Seeds; Tapioca; Tea; Thyme; Tomato; Trout; Tuna Mix; Turkey; Turnip; Vanilla; Walnut Food, Black; Walnut Food, English; Watermelon; Wheat, Whole (Grain) Whitefish; Yeast, Bakers; Yeast, Brewers; Yeast Mix (Bakers/Brewers, Sacchoromyces cerevisiae).

EXAMPLE 7

Repeating the procedure of Example 1 with allergens derived from each of the following molds provides a microtiter well to which the corresponding allergen is adhered: *Alternaria tenuis; Aspergillus clavatus; Aspergillus fumigatus; Aspergillus glaucus; Aspergillus nidulans; Aspergillus niger; Aspergillus restrictus; Aspergillus sydowi; Aspergillus terreus; Botrytis cinerea; Candida albicans; Cephalosporium acremonium; Cephalothecium (Tricho-*

*thecium) reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum (Cladosporium); Monilia sitophila; Mucor racemosus; Mycogone sp.; Neurospora crassa; Nigrospora sphaerica; Oidiodendrm sp.; Paecilomyces varioti; Penicillium artramentosum; Penicillium biforme; Penicillium carminoviolaceum; Penicillium chrysogenum; Penicillium digitatum; Penicillium expansum; Penicillium glaucum; Penicillium intricatum; Penicillium luteum; Penicillium notatum; Penicillium roqueforti; Penicillium roseum; Phoma herbarum; Pleospora sp.; Poria sp.; Pullularia pullulans; Rhizopus nigricans; Rhodotorula glutinis; Saccharomyces cerevisiae* (See Yeast Mix); *Scopulariopsis brevicaulis; Spondylocladium sp.; Sporobolomyces salmonicolor; Stemphylium botryosum; Streptomyces griseus; Trichoderma viride; Typhula idahoensis; Verticillum alboatrum.*

EXAMPLE 8

Repeating the procedure of Example 1 with allergens derived from each of the following smuts provides a microtiter well to which the corresponding allergen is adhered: Smut, Barley; Smut, Bermuda; Smut Corn; Smut, Johnson; Smut, Oat; Smut, Sorghum; Smut, Wheat.

EXAMPLE 9

Repeating the procedure of Example 1 with allergens derived from each of the following insects and insect venoms provides a microtiter plate to which the corresponding allergen is adhered: Ants, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea antigen; Fruit Flies; Gnat sp.; Horney, Black and Yellow; Horse Fly; House Fly; Mayfly sp.; Mite (D. farinae); Mosquito Mix; Moth, Miller; Wasp; Yellow Jacket; Honey Bee Venom Protein—*Apis mellifera*; Wasp Venom Protein—*Polistes sp.*; White-faced Horner Venom Protein—*Dolichovespula maculata*; Yellow Hornet Venom Protein—*Dolichovespula arenaria*; Yellow Jacket Venom Protein—*Vespula sp.*; Mixed Vespid Venom Protein.

EXAMPLE 10

The product of Example 1, a microtiter plate well to which perennial ryegrass pollen allergen is adhered, is washed 3 times with 0.9% sodium chloride rinse solution containing 0.05% Tween 20 (polyoxyethylene sorbitan monooleate). Patient serum of a patient suffering an allergy to perennial ryegrass pollen (100 microtiters) is added to the well and inoculated at room temperature for 2 hr. The well is aspirated and washed 3 times with the above saline rinse solution.

Then 100 microtiters of solution containing one microgram of alkaline phosphatase labeled monoclonal anti-IgE antibody in a PBS solution containing 4%(w/v) polyethylene glycol 4000 and 0.05% Tween 20, is added to the well and incubated for 2 hr at room temperature. The well is then aspirated and washed 3 times with the above rinse solution.

Then 100 microtiters of an aqueous $10^{-4}$M 4-methylumbelliferyl phosphate solution containing 1.25M 2-amino- 2-methyl-1-propanol buffer and 0.125 mM. magnesium chloride, pH 9.6, is added to the well and incubated for 60 minutes at room temperature. The fluorescence level is read with a fluorometer with excitation at 365 nm and the reading at 450 nm.

The invention claimed is:

1. A method for identifying and quantifying allergen specific IgE levels in patient serum comprising:
    (a) contacting an insoluble support having allergen adhering thereto with patient serum for a sufficient time to permit conjugation of any allegen specific IgE to the allergen and removing the patient serum therefrom;
    (b) contacting the insoluble support with anti-IgE antibody labeled with a fluorogenic enzyme for a time between 30 and 180 minutes and sufficient to permit conjugation of the anti-IgE antibody to any IgE and removing any non-bound anti-IgE antibody therefrom;
    (c) contacting the insoluble support with a solution of substrate which undergoes reaction in the presence of the fluorogenic enzyme to yield fluorescent product for a period between 5 and 240 minutes;
    (d) measuring the fluorescence level of the solution; and
    (e) determining the amount of allergen specific IgE in the patient serum by comparing the fluorescence measured in step d with those of control solutions 2. The method of claim 1 wherein the insoluble support is a test well and the test well is separated from other test wells by opaque material.

3. The method of claim 1 wherein the insoluble support is contacted with anti-IgE antibody labelled with fluorogenic enzyme in an aqueous solution containing from 1 to 8 wt. % polyethylene glycol having a molecular weight within the range of from 1,000 to 10,000.

4. The method of claim 2 wherein the well is made of opaque material.

5. The method of claim 4 wherein the anti-IgE antibody is a monoclonal antibody.

6. The method of claim 4 wherein the anti-IgE antibody is labeled with alkaline phosphatase.

7. The method of claim 6 wherein the substrate is 4-methylumbelliferyl phosphate.

8. The method of claim 2 wherein the allergen is derived from a pollen, mold, smut, animal dander or epidermal, insect, insect venom, dust or food.

* * * * *

UNITED STATES PATENT AND TRADEMARK OFFICE
CERTIFICATE OF CORRECTION

PATENT NO. : B1 4,845,027

DATED : May 10, 1994

INVENTOR(S) : Calenoff *et al.*

It is certified that error appears in the above-identified patent and that said Letters Patent is hereby corrected as shown below:

On the title page, item [73] Assingee:

In the name of the assignee:

"Biowhittraker, Inc." should read --BioWhittaker, Inc.
Walkersville, Maryland--.

After item [73] Assignee:

In the data relating to the Reexamination Certificate:

"Patent No.: 4,845,027
Issued: Jan. 15, 1988
Appl. No.: 144,737
Filed: Jul. 4, 1989" should read --Patent No.: 4,845,027
Issued: Jul. 4, 1989
Appl. No.: 144,737
Filed: Jan. 15, 1988--.

UNITED STATES PATENT AND TRADEMARK OFFICE
CERTIFICATE OF CORRECTION

PATENT NO. : B1 4,845,027
DATED : May 10, 1994
INVENTOR(S) : Calenoff et al

It is certified that error appears in the above-indentified patent and that said Letters Patent is hereby corrected as shown below:

In item [63] Related U.S. Application Data:
"October 13, 1992" should read --October 13, 1987--.

Signed and Sealed this

Thirtieth Day of August, 1994

Attest:

BRUCE LEHMAN

Attesting Officer     Commissioner of Patents and Trademarks

REEXAMINATION CERTIFICATE (2295th)

United States Patent [19]

Calenoff et al.

[11] B1 4,845,027

[45] Certificate Issued May 10, 1994

[54] FLUOROMETRIC ASSAY OF ALLERGIC REACTIONS

[75] Inventors: Emanuel Calenoff, Burlingame; Ruth M. Johnson, Redwood City; Yuh-Geng Tsay, San Jose; John Scott, Mountain View, all of Calif.

[73] Assignee: Biowhittraker, Inc.

Reexamination Request:
No. 90/003,001, Mar. 8, 1993

Reexamination Certificate for:
| | |
|---|---|
| Patent No.: | 4,845,027 |
| Issued: | Jan. 15, 1988 |
| Appl. No.: | 144,737 |
| Filed: | Jul. 4, 1989 |

Related U.S. Application Data

[63] Continuation of Ser. No. 434,061, Oct. 13, 1992, abandoned.

[51] Int. Cl.$^5$ .................... G01N 33/53; G01N 33/535
[52] U.S. Cl. .................... 435/7.95; 435/7.21; 435/7.31; 435/21; 435/968; 436/513; 436/809
[58] Field of Search ............... 436/513; 435/7.9, 7.92, 435/21, 968

[56] References Cited

U.S. PATENT DOCUMENTS

| | | | |
|---|---|---|---|
| Re. 29,169 | 4/1977 | Schuurs et al. | 195/103.5 A |
| Re. 29,474 | 11/1977 | Axen et al. | 424/1 |
| Re. 31,006 | 8/1982 | Schuurs et al. | 435/188 |
| 3,551,555 | 12/1970 | Schuurs | 424/12 |
| 3,553,310 | 1/1971 | Csizmas et al. | 424/2 |
| 3,555,143 | 1/1971 | Axen et al. | 424/1 |
| 3,720,760 | 3/1973 | Bennich et al. | 424/1 |
| 3,839,153 | 10/1974 | Schuurs et al. | 195/103.5 A |
| 3,941,876 | 3/1976 | Marinkovich | 424/1 |
| 3,966,898 | 2/1976 | Sjoquist et al. | 424/12 |
| 4,002,532 | 1/1977 | Weltman et al. | 195/103.5 A |
| 4,048,298 | 9/1977 | Niswender | 424/1.5 |
| 4,092,408 | 5/1978 | Litt | 424/1 |
| 4,190,496 | 2/1980 | Rubenstein et al. | 435/7.9 |
| 4,210,418 | 7/1980 | Brown et al. | 23/230 B |
| 4,211,762 | 7/1980 | Huggins et al. | 424/1 |
| 4,240,751 | 12/1980 | Linnecke et al. | 356/409 |
| 4,298,592 | 11/1981 | Lin et al. | 424/1 |
| 4,331,650 | 5/1982 | Brewer et al. | 424/12 |
| 4,347,311 | 8/1982 | Schmitz | 435/5 |
| 4,376,110 | 3/1983 | David et al. | 436/513 |
| 4,410,634 | 10/1983 | Cooper et al. | 436/500 |
| 4,444,879 | 4/1989 | Foster et al. | 436/513 |
| 4,450,231 | 5/1984 | Ozkan | 436/538 |
| 4,471,058 | 8/1984 | Smith et al. | 536/518 |
| 4,501,970 | 2/1985 | Nelson | 250/458.1 |
| 4,539,292 | 9/1985 | Reid et al. | 436/513 |
| 4,725,388 | 2/1988 | Nelson et al. | 264/21 |
| 4,844,966 | 7/1989 | Calenoff et al. | 436/513 |
| 4,849,337 | 7/1989 | Calenoff et al. | 436/513 |

FOREIGN PATENT DOCUMENTS

| | | |
|---|---|---|
| 106662 | 10/1983 | European Pat. Off. |
| 2556840 | 12/1983 | France |
| 53-35126 | 9/1978 | Japan |
| 54-46827 | 4/1979 | Japan |
| 54-134694 | 10/1979 | Japan |
| 55-22186 | 2/1980 | Japan |
| 55-30655 | 3/1980 | Japan |
| 55-135752 | 10/1980 | Japan |
| 56-21598 | 2/1981 | Japan |
| 58-16698 | 1/1983 | Japan |

OTHER PUBLICATIONS

Ishikawa et al., Eds. "IgE" In: *Enzyme Immunoassay*, 1978, pp. 173–179.

Deelder et al., 1980, *Journal Immunolological Methods*, 36:269–283.

Ishikawa and Kato, 1978, *Scand. J. Immunol.*, 8 (suppl. 7):43–55.

Brochure, revised Jan. 1981, for Pharmacia Diagnostics Phadebas RAST ® assay.

Pharmacia Diagnostics 1983 Catalog.

Brochure, Oct. 1983, for Pharmacia Diagnostics Phadebas RAST ® Radioimmunoassay.

Male, David, *Immunology: An Illustrated Outline* p. 24, Gower Medical Publishing, 1986.

Savory and Buffone, In: *Automated Immunoanalysis*, Part 2, Ritchie, ed., 1978, Marcel Dekker, Inc., pp. 335–343.

Bruynzeel and Berrens, 1979, *Int. Archs Allergy appl. Immun.*, 58:344–350.

Maggio, ed., *In: Enzyme-Immunoassay*, 1980, CRC Press, Inc., pp. 26, 173-176 and 198-199.
Shalev et al., *J. Immunol. Meth.*, 1980, 38:125-139.
Goldsmith, *Analyt. Biochem.*, 1981, 117:53-60.
Cheung et al., 1981, *Annals of Allergy*, 46:132-136.
Iskander et al., 1981, *Int. Archs Allergy appl. Immun.*, 66:200-207.
Kramps et al., 1981, *Int. Archs Allergy appl. Immun.*, 64:428-438.

*Primary Examiner*—Toni R. Scheiner

[57] ABSTRACT

A method for identifying and quantifying allergen specific IgE levels in patient serum by conjugating the serum IgE with allergens on an insoluble support, conjugating the serum IgE with an enzyme labeled anti-IgE antibody, contacting the enzyme with a solution of a substrate which will yield a fluorescent product in the presence of the enzyme, and measuring the level of fluoresence in the solution.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

New claims 9 and 10 are added and determined to be patentable.

9. *The method of claim 1 wherein the anti-IgE antibody is a monoclonal antibody.*

10. *The method of claim 1 wherein the allergen is derived from a pollen, mold, smut, animal dander or eqidermal, insect, insect venom, dust or food.*

* * * * *